(12) United States Patent
Simonnet et al.

(10) Patent No.: US 9,364,411 B2
(45) Date of Patent: Jun. 14, 2016

(54) USE OF MONOSACCHARIDES AND COMPOSITION THEREFOR

(75) Inventors: Jean-Thierry Simonnet, Cachan (FR); Julien Laboureau, Issy les Moulinaux (FR); Pascal Portes, Nogent sur Marne (FR); Christophe Boulle, Paris (FR)

(73) Assignee: L'OREAL, Paris (FR)

( * ) Notice: Subject to any disclaimer, the term of this patent is extended or adjusted under 35 U.S.C. 154(b) by 437 days.

(21) Appl. No.: 12/648,485

(22) Filed: Dec. 29, 2009

(65) Prior Publication Data

US 2010/0190727 A1 Jul. 29, 2010

Related U.S. Application Data

(60) Provisional application No. 61/144,774, filed on Jan. 15, 2009.

(30) Foreign Application Priority Data

Dec. 30, 2008 (FR) ...................................... 08 59147

(51) Int. Cl.
| | | |
|---|---|---|
| A61K 31/7004 | (2006.01) |
| C07H 1/00 | (2006.01) |
| A61K 8/60 | (2006.01) |
| A61K 8/02 | (2006.01) |
| A61Q 5/12 | (2006.01) |
| A61Q 7/00 | (2006.01) |
| A61Q 19/08 | (2006.01) |

(52) U.S. Cl.
CPC ... *A61K 8/60* (2013.01); *A61K 8/02* (2013.01); *A61Q 5/12* (2013.01); *A61Q 7/00* (2013.01); *A61Q 19/08* (2013.01); *A61K 2800/91* (2013.01)

(58) Field of Classification Search
USPC ........................................... 514/23; 536/1.11
See application file for complete search history.

(56) References Cited

U.S. PATENT DOCUMENTS

| | | | | |
|---|---|---|---|---|
| 4,518,517 A * | 5/1985 | Eigen et al. ................ | 510/131 |
| 6,403,108 B1 * | 6/2002 | Abdullah ...................... | 424/401 |
| 6,565,532 B1 * | 5/2003 | Yuzhakov et al. ............ | 604/142 |
| 7,297,355 B2 * | 11/2007 | Fleury Rey et al. ............ | 426/62 |
| 8,110,209 B2 * | 2/2012 | Prestrelski et al. ............ | 424/423 |
| 2006/0115443 A1 | 6/2006 | Gesztesi et al. | |
| 2007/0025933 A1 | 2/2007 | Guerrero Gomez-Pamo et al. | |
| 2010/0009931 A1 | 1/2010 | Laboureau et al. | |

FOREIGN PATENT DOCUMENTS

| | | |
|---|---|---|
| CN | 101095688 | 1/2008 |
| DE | 196 03 423 | 8/1996 |
| DE | 197 04 693 | 8/1998 |
| FR | 2 609 397 | 7/1988 |
| FR | 2 756 735 | 6/1998 |
| FR | 2 768 623 | 3/1999 |
| FR | 2 773 324 | 7/1999 |
| FR | 2 853 539 | 10/2004 |
| FR | 2 876 283 | 4/2006 |
| FR | 2 900 574 | 11/2007 |
| JP | 11199430 A * | 7/1999 |
| JP | 2001163720 A * | 6/2001 |
| JP | 2001278769 A * | 10/2001 |
| JP | 2004262861 A * | 9/2015 |
| WO | WO 2007/007095 A2 | 1/2007 |
| WO | WO 2007/101493 | 9/2007 |
| WO | 2007/128939 | 11/2007 |
| WO | WO 2008/148966 | 12/2008 |

OTHER PUBLICATIONS

Akiyoshi et al.; JP 2001163720 A; Jun. 19, 2001 ( Machine English Translation).*
Hayashi et al. ; JP 11335226 A; Dec. 7, 1999 (Machine English Translation).*
STN Abstract of Hayashi et al. ; JP 11335226 A; Dec. 7, 1999 (Abstract sent).*
Noel; FR2756735 A1; Jun. 12, 1998 (Machine English Translation).*
Ogawa et al. (JP 11199430 A; Jul. 27, 1999 (Machine English Translation).*
STN Abstract of Ogawa et al. (JP 11199430 A; Jul. 27, 1999 (Abstract sent).*
Laboureau et al.; WO 2007/128939 A2; Nov. 15, 2007 (Machine English Translation).*
Handa; JP 2004262861 A; Sep. 24, 2004 (Machine EnglishTranslation).*
Fujimura et al.; JP 2001278769 A; Oct. 10, 2001 (Machine English Translation).*
U.S. Appl. No. 12/649,367, filed Dec. 30, 2009, Laboureau, et al.
U.S. Appl. No. 12/649,372, filed Dec. 30, 2009, Laboureau, et al.
U.S. Appl. No. 12/649,370, filed Dec. 30, 2009, Laboureau, et al.
U.S. Appl. No. 12/649,366, filed Dec. 30, 2009, Laboureau, et al.
U.S. Appl. No. 12/649,415, filed Dec. 30, 2009, Laboureau, et al.
U.S. Appl. No. 12/649,368, filed Dec. 30, 2009, Laboureau, et al.
Office Action as received in the corresponding Korean Patent Application No. 10-2009-0132864 dated Sep. 27, 2012 w/English Translation.
Database GNPD [Online] Mintel; Jul. 1, 2007, Anonymous: "Very High Protection Cream", extract of www.gnpd.com. database accession No. 738326.
Office Action issued Apr. 10, 2013 in European Application No. 09 181 013.5.
Office Action as received in the corresponding Chinese Patent Application No. 200910265296.9 dated Jun. 16, 2011.

* cited by examiner

*Primary Examiner* — Shaojia Anna Jiang
*Assistant Examiner* — Michael C Henry
(74) *Attorney, Agent, or Firm* — Oblon, McClelland, Maier & Neustadt, L.L.P.

(57) ABSTRACT

The present invention relates to the use, especially the cosmetic use, of at least one monosaccharide chosen from mannose, rhamnose and a mixture thereof, for reducing or preventing the signs of ageing of the skin or its integuments. The present invention also relates to a cosmetic composition and a device containing it.

2 Claims, 3 Drawing Sheets

USE OF MONOSACCHARIDES AND COMPOSITION THEREFOR

REFERENCE TO PRIOR APPLICATIONS

This application claims priority to U.S. provisional application Ser. No. 61/144,774, filed Jan. 15, 2009; and to French patent application 08 59147, filed Dec. 30, 2008, both incorporated herein by reference.

FIELD OF THE INVENTION

The present invention relates to the use, especially the cosmetic and/or dermatological use, of at least one monosaccharide selected from mannose, rhamnose and a mixture thereof, for reducing or preventing the signs of ageing of the skin or its integuments. The present invention also relates to a cosmetic composition comprising, in a physiologically acceptable medium, at least one monosaccharide selected from mannose, rhamnose and a mixture thereof, and also to a device containing it.

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. The description is to be regarded as illustrative in nature, and not as restrictive.

BACKGROUND OF THE INVENTION

Human skin is made up of two main layers, namely the dermis and the epidermis that superficially covers the dermis. Natural human epidermis is composed mainly of three types of cells, namely keratinocytes, which form the vast majority, melanocytes and Langerhans cells. Each of these three types of cells contributes, via its intrinsic functions, to the essential role played in the body by the skin, especially the role of protecting the body against external attacking factors (the climate, ultraviolet rays, tobacco, etc.), which is also known as the "barrier function".

The epidermis is a keratinized, stratified pavement epithelium 90% formed from keratinocytes. The gradual differentiation of the cells of the basal membrane, which separates the dermis from the epidermis, towards the surface of the epidermis especially includes the differentiation of keratinocytes, which migrate towards the surface of the skin, where they desquamate.

Ageing of the epidermis is manifested mainly by a reduction in its thickness. Atrophy of the epidermis is the consequence of the slowing down of keratinocyte proliferation and of the accumulation of senescent keratinocytes. The horny layer becomes dull.

The dermis provides the epidermis with a solid support. It is also its nourishing element. It is made up mainly of fibroblasts and an extracellular matrix composed mainly of collagen, elastin and a substance known as ground substance. These components are synthesized by the fibroblasts. The cohesion between the epidermis and the dermis is provided by the dermo-epidermal junction. This is a complex region about 100 nm thick, which comprises the basal pole of the basal keratinocytes, the epidermal membrane and the sub-basal zone of the superficial dermis.

Collagens are the major proteins of the extracellular matrices of the skin. To date, 20 types of collagen have been identified, and are noted from I to XX. The collagens predominantly present throughout the epidermis are collagens of the type I and III that form the extracellular matrix of the entire dermis (these collagens constitute 70-80% of the dry weight of the dermis). Moreover, collagens are not all synthesized by the same cell types: collagens of type I and III are essentially produced by the dermal fibroblasts, whereas type VII collagen is produced by two categories of cell, keratinocytes and fibroblasts. Regulation of their expression differs from one collagen to another, for example collagens I and VII are not regulated in the same way by certain cytokines; specifically, TNF-α and leukoregulin stimulate collagen VII and negatively regulate collagen I. Finally, all collagen molecules are variants of a common precursor, which is the α chain of procollagen.

With age, collagen becomes thinner and wrinkles appear on the surface of the skin. Cutaneous ageing is a genetically programmed mechanism.

Moreover, certain environmental factors such as smoking and exposure to sunlight accelerate it. The skin thus has a much more aged appearance on the areas exposed to sunlight, such as the back of the hands or the face. Thus, these other factors also have a negative impact on the natural collagen of the skin.

Consequently, given the important role of collagen in the integrity of the skin and in its resistance to external attacking factors of mechanical type, stimulation of the synthesis of these collagens, and in particular of type I collagen, appears to be an effective means for overcoming the signs of ageing of the skin. During chronological ageing, the epidermis also undergoes many modifications and degradations that are reflected, with age, by an impairment in the microrelief, associated with an impairment in the barrier function of the skin, the appearance of wrinkles and fine lines, an impairment in the mechanical properties of the skin, especially lack of elasticity of the skin, and loss of radiance of the complexion.

The importance of having available products whose effects are directed towards regenerating skin tissue via increasing keratinocyte proliferation and stimulating fibroblast proliferation and/or metabolism, and especially stimulating collagen synthesis, may thus be appreciated.

It is known practice from the literature to use agents such as retinol, which promote keratinocyte proliferation and can stimulate epidermal renewal and maintain and/or increase the thickness of the epidermis: this is then referred to as a direct biological effect. However, retinol has a certain number of drawbacks when it is used in a cosmetic composition. Specifically, it has low stability towards oxidation and gives rise to adverse side effects on consumers, especially such as skin irritation. There is thus a need to find other compounds with a direct biological effect, which are readily available and whose efficacy is acceptable for optimal use in cosmetics.

DETAILED DESCRIPTION OF THE PREFERRED EMBODIMENTS

The present invention has demonstrated, surprisingly and unexpectedly, that monosaccharides chosen from mannose, rhamnose and a mixture thereof have the activity desired in this context, and as regards the imposed constraints mentioned in the preceding paragraph.

Thus, the inventors have found that mannose and/or rhamnose are capable of increasing the number of keratinocytes and/or fibroblasts, of stimulating fibroblast metabolism, by stimulating collagen synthesis, in particular the synthesis of type 1 procollagen; and thus of counteracting the signs of ageing of the skin, and in particular age-related epidermal and/or dermal atrophy.

The use of these monosaccharides for the direct biological effects outlined above was hitherto unknown. Patent application WO 2007/128939 mentions anti-ageing activity obtained via a biomechanical effect of a tensioning agent in combination with saccharide compounds, which makes it possible to increase the expression of the skin cell mechanoreceptors. This increase in the expression of mechanoreceptors is described as increasing the sensitization of skin cells to respond to the effects of tensioning agents. Similarly, French patent application FR 2900572 mentions a skincare cosmetic process involving the combined use of a composition comprising a saccharide compound that can increase the expression of skin cell mechanoreceptors, and of a device intended for applying mechanical constraints to the skin, which allows the efficacy of the mechanical constraints to be increased by means of increasing the number of skin cell mechanoreceptors.

Patent application US 2007/0025933 discloses a composition comprising a photoprotector base made up of two types of components, and optionally a mixture of additional components, such as for instance monosaccharides (like mannose, fructose and glucose) and acids of the Krebs cycle or derivatives thereof (like citric, malic, fumaric acid) which contribute to the stability of the composition. No activity on the skin specific to the monosaccharides is disclosed.

Patent application WO 2005/063194 describes a galenical base with very high tolerance especially comprising mannose or rhamnose. It is specified that such a galenical base can function only in combination with an active agent whose galenical base is only the vehicle. The dermal and/or cosmetic galenical bases disclosed are based essentially on the presence of the two polyols, namely mannitol and xylitol.

Mannose is a hexose that is the C2 epimer of glucose. Rhamnose (or 6-deoxymannose) formally constitutes the product of deoxygenation of mannose at C6. The monosaccharides according to the invention are in the D or L form of mannose and/or rhamnose or a mixture thereof, each form itself possibly being the alpha and/or beta anomer. The forms that are preferred according to the invention are D-mannose or L-rhamnose.

D-Mannose is present in plants, in particular certain fruit, including cranberries, or in hardwood (beech and birch). Rhamnose is found in nature in L form. D-Mannose and L-rhamnose are commercially available, for example from the company Danisco Sweeteners® or from the company Symrise.

In the present invention, the monosaccharide is preferably present as a monomer.

The present invention thus relates in one embodiment to the use, especially the cosmetic or dermatological use, of at least one monosaccharide selected from mannose, rhamnose and a mixture thereof, for reducing or preventing the signs of ageing of the skin or its integuments, for increasing keratinocyte and/or fibroblast proliferation and/or for stimulating collagen synthesis.

According to one particular aspect, the invention relates to the use, especially the cosmetic or dermatological use, of at least one monosaccharide chosen from mannose, rhamnose and a mixture thereof, for stimulating regeneration of the skin, in particular of the epidermis and/or the dermis, by means of better cell renewal of the skin, in particular of the epidermis and/or the dermis.

The monosaccharide according to the invention makes it possible to stimulate the regeneration of epidermal and dermal cells, in the skin or the integuments, in particular keratinocytes and fibroblasts, by increasing their proliferation. This therefore provides a method, especially a cosmetic method, which is especially effective for combating the signs of ageing, more specifically of chronological ageing. The signs of chronological ageing correspond to internal degradations of the skin due to the intrinsic ageing of the individuals.

The active agent, namely the monosaccharide as defined above, makes it possible to maintain and/or reinforce the epidermis and/or the dermis, and to maintain the integrity and/or thickness of the various layers of the skin, and in particular the epidermis and/or the dermis. It also makes it possible to maintain the elasticity and tonicity of the skin.

Another aspect of the invention concerns the cosmetic and/or dermatological use of at least one monosaccharide chosen from mannose, rhamnose and a mixture thereof, for preventively or curatively treating the signs of ageing of the skin, in particular of the body or the face, in particular the chronobiological signs of ageing of the skin, and especially ageing caused by a decrease in skin elasticity and/or by a degradation of the collagen in the structure of tissues.

Another object of the invention is the use of at least one monosaccharide chosen from mannose, rhamnose and a mixture thereof, for preventively or curatively treating, or for reducing or preventing, wrinkles and/or fine lines, withered skin, lack of skin elasticity and/or tonicity, thinning of the dermis, degradation of collagen fibres, flaccid skin, thinned skin or any internal degradation of the skin.

Another object of the invention is the use of at least one monosaccharide chosen from mannose, rhamnose and a mixture thereof, for maintaining and/or improving the barrier function of the skin.

Another object of the invention is the use of at least one monosaccharide chosen from mannose, rhamnose and a mixture thereof, for maintaining the radiance of the skin and/or for making the skin radiant.

The invention also relates to the use, especially the cosmetic use, of at least one monosaccharide chosen from mannose, rhamnose and a mixture thereof, for improving and/or reducing the microrelief of the skin or for maintaining and/or improving the barrier function of the skin.

The use of the monosaccharide in accordance with the invention makes it possible to efficiently combat the signs of ageing of body or facial skin. The monosaccharide according to the invention can thus preventively or curatively treat wrinkles and/or fine lines. The monosaccharide according to the invention can also retard or prevent the appearance of wrinkles and/or fine lines.

More specifically, the present invention relates to the cosmetic use of at least one monosaccharide chosen from mannose, rhamnose and a mixture thereof, for preventively or curatively treating wrinkles and/or fine lines, and/or any internal degradation of the skin.

The present invention also relates to the cosmetic use of at least one monosaccharide chosen from mannose, rhamnose and a mixture thereof, for maintaining and/or reinforcing the epidermis and/or the dermis, or for maintaining the integrity and/or thickness of the various layers of the epidermis and of the dermis.

The monosaccharide according to the invention may be administered orally, topically to the skin or its integuments, or via cutaneous injection.

More specifically, mannose, rhamnose or a mixture thereof are used as active agent in a cosmetic or dermatological composition.

The present invention also relates to the use of at least one monosaccharide chosen from mannose, rhamnose and a mixture thereof, administered orally, topically or via cutaneous injection, especially for skin and/or scalp care.

A haircare cosmetic composition in accordance with the invention comprising at least one monosaccharide chosen from mannose, rhamnose and a mixture thereof can in particular stimulate growth of the hair, combat hair loss, slow down its loss or reinforce the radiance of the hair.

Moreover, the present invention relates to a cosmetic and/or dermatological composition comprising, in a physiologically acceptable medium, at least one monosaccharide chosen from mannose, rhamnose and a mixture thereof, the said composition not comprising any tensioning agent and not comprising a combination of xylitol and mannitol.

Thus, the composition according to the invention may be intended for the uses as described previously.

The monosaccharide according to the invention is more particularly present in the composition according to the invention as active agent (or active ingredient), in particular as sole active agent.

The terms "active agent" and "active ingredient" more specifically mean according to the invention a compound which, when administered to an individual, in particular a human individual, plays a direct biological role on the body, in particular on the skin or its integuments, in particular without improving the biological or mechanical effect of another compound present in the composition according to the invention.

More particularly, the composition according to the invention does not comprise any additional monosaccharide.

According to the invention, the term "tensioning agent" generally means any polymer that is soluble or dispersible in water at a temperature ranging from 25° C. to 50° C. at a concentration of 7% by weight in water or at the maximum concentration at which a medium of uniform appearance is formed and producing at this concentration of 7% or at this maximum concentration in water a shrinkage of more than 15% in the test described below.

The maximum concentration at which a medium of uniform appearance forms is determined to within ±20% and preferably to within ±5%.

The expression "medium of uniform appearance" means a medium that does not contain any aggregates that are visible to the naked eye.

For the determination of the said maximum concentration, the tensioning agent is gradually added to the water with deflocculating stirring at a temperature ranging from 25° C. to 50° C., and the mixture is then stirred for one hour. The mixture thus prepared is then examined after 24 hours to see if it is of uniform appearance (absence of aggregates visible to the naked eye).

The tensioning effect may be characterized by an in vitro shrinkage test.

A homogeneous mixture of the tensioning agent in water, at a concentration of 7% by weight or at the maximum concentration defined above, is prepared beforehand and as described previously.

30 μl of the homogeneous mixture are placed on a rectangular sample (10×40 mm, thus having an initial width $L_0$ of 10 mm) of elastomer with a modulus of elasticity of 20 MPa and a thickness of 100 μm.

After drying for 3 hours at 22±3° C. and 40±10% relative humidity RH, the elastomer sample has a shrunken width, noted $L_{3h}$, due to the tension exerted by the applied tensioning agent.

The tensioning effect (TE) of the said polymer is then quantified in the following manner:

$$'TE' = (L_0 - L_{3h}/L_0) \times 100 \text{ as \%}$$

with $L_0$=initial width 10 mm and
$L_{3h}$=width after 3 hours of drying
The tensioning agent may be chosen from:
a) plant or animal proteins and hydrolysates thereof;
b) polysaccharides of natural origin;
c) mixed silicates;
d) colloidal particles of mineral fillers;
e) synthetic polymers;
and mixtures thereof.

A person skilled in the art will know how to choose, from the chemical categories listed above, the materials corresponding to the test as described previously.

The present invention also relates to a composition comprising mannose and/or rhamnose, which is suitable for topical administration, advantageously being in the form of a cream, a gel, a lotion, a milk, an oil, an ointment, a wax, a mousse, a paste, a serum, a pomade or a shampoo.

The monosaccharide according to the invention, namely mannose and/or rhamnose, and in particular rhamnose, is also advantageously used for treating (or for the preparation of pharmaceutical compositions for treating) skin disorders associated with abnormally low proliferation of epidermal or dermal cells, in particular keratinocytes or fibroblasts. The monosaccharide according to the invention may be used for treating (or for the preparation of pharmaceutical compositions for treating) skin disorders associated with a reduction in the level of collagen. In particular, the said disorders are such as those identified above. The composition may be intended for reducing or preventing the signs of ageing of the skin or its integuments, in particular by increasing keratinocyte or fibroblast proliferation and/or by stimulating the synthesis of collagen, and in particular of type I collagen. Preferably, the pharmaceutical composition is a dermatological composition.

A object of the present invention is also a treatment method, in particular a cosmetic or therapeutic treatment method, for reducing or preventing the signs of ageing of the skin or its integuments, by administration to an individual, preferably a human being, of an effective amount of at least one monosaccharide as defined previously or of a composition according to the invention.

The amount of monosaccharide to be used according to the invention depends on the desired cosmetic or therapeutic effect, and may thus vary within a wide range.

A person skilled in the art can, on the basis of his general knowledge, readily determine the appropriate amounts.

A composition according to the invention may comprise at least one monosaccharide as defined above in an amount of between 0.001% and 30% by weight relative to the total weight of the composition, in particular between 0.1% and 10% by weight and more particularly between 0.5% and 6% by weight relative to the total weight of the composition.

The composition according to the invention comprises at least one monosaccharide as defined previously in combination with a physiologically acceptable medium, in particular a cosmetically or pharmaceutically acceptable medium.

In general, this medium may be anhydrous or aqueous. It may thus comprise an aqueous phase and/or a fatty phase.

The physiologically acceptable medium in which the compounds according to the invention may be employed, and also the constituents thereof, their amount, the galenical form of the composition, its mode of preparation and its mode of administration, may be chosen by a person skilled in the art on the basis of his general knowledge, as a function of the desired type of composition.

When the composition is a composition intended for topical administration, it may advantageously be in the form of aqueous or aqueous-alcoholic solutions, oil-in-water (O/W) or water-in-oil (W/O) emulsions or multiple emulsions (triple: W/O/W or O/W/O), nanoemulsions, in particular O/W nanoemulsions, in which the size of the drops is less than 100 nm, aqueous gels, or dispersions of a fatty phase in an aqueous phase with the aid of spherules, these spherules possibly being polymer nanoparticles such as nanospheres and nanocapsules or lipid vesicles of ionic and/or nonionic type (liposomes, niosomes or oleosomes).

These compositions are prepared according to the usual methods.

In addition, the compositions that may be used according to the invention may be more or less fluid and may have the appearance of a white or coloured cream, a pomade, a milk, a lotion, a serum, a paste or a mousse. They may optionally be applied to the skin in aerosol form. They may also be in solid form, for example in stick form.

For local application to the hair or the scalp, the composition may be in the form of aqueous, alcoholic or aqueous-alcoholic solutions; in the form of creams, gels, emulsions or mousses; in the form of aerosol compositions also comprising a propellant under pressure.

When the composition is in aqueous form, especially in the form of an aqueous dispersion, emulsion or solution, it may comprise an aqueous phase, which may comprise water, a floral water and/or a mineral water.

When the composition is an emulsion, the proportion of the fatty phase may range from about 5% to 80% by weight and preferably from about 2% to 50% by weight relative to the total weight of the composition. The oils, waxes, emulsifiers and co-emulsifiers used in the composition in emulsion form are chosen from those conventionally used in cosmetics. The emulsifier and the co-emulsifier are present in the composition in a proportion ranging from 0.3% to 30% by weight and preferably from 0.5% to 20% by weight relative to the total weight of the composition. The emulsion may also contain lipid vesicles.

When the composition is an oily solution or gel, the fatty phase may represent more than 90% of the total weight of the composition.

The oily phase may also comprise any common liposoluble or lipodispersible additive, as indicated hereinbelow.

It may especially comprise fatty substances such as waxes, pasty compounds, fatty alcohols or fatty acids. The oily phase contains at least one oil, more particularly at least one cosmetic oil. The term "oil" means a fatty substance that is liquid at room temperature (25° C.).

As oils that may be used in the composition of the invention, examples that may be mentioned include:

hydrocarbon-based oils of animal origin, such as perhydrosqualene;

hydrocarbon-based oils of plant origin, such as liquid triglycerides of fatty acids containing from 4 to 10 carbon atoms, for instance heptanoic or octanoic acid triglycerides, or alternatively, for example, sunflower oil, corn oil, soybean oil, marrow oil, grapeseed oil, sesameseed oil, hazelnut oil, apricot oil, macadamia oil, arara oil, coriander oil, castor oil, avocado oil, caprylic/capric acid triglycerides, for instance those sold by the company Stearineries Dubois or those sold under the names Miglyol 810, 812 and 818 by the company Dynamit Nobel, jojoba oil, shea butter oil and caprylyl glycol;

synthetic esters and ethers, especially of fatty acids, for instance the oils of formulae $R^1COOR^2$ and $R^1R^2$ in which $R^1$ represents a fatty acid or a fatty alcohol residue containing from 8 to 29 carbon atoms and $R^2$ represents a branched or unbranched hydrocarbon-based chain containing from 3 to 30 carbon atoms, for instance Purcellin oil, 2-octyldodecyl stearate, 2-octyldodecyl erucate, isostearyl isostearate; hydroxylated esters, for instance isostearyl lactate, octyl hydroxystearate, octyldodecyl hydroxystearate, diisostearyl malate or triisocetyl citrate; fatty alcohol heptanoates, octanoates or decanoates; polyol esters, for instance propylene glycol dioctanoate, neopentyl glycol diheptanoate and diethylene glycol diisononanoate; and pentaerythritol esters, for instance pentaerythrityl tetraisostearate, or isopropyl lauroyl sarcosinate, sold especially under the trade name Eldew SL 205 by the company Ajinomoto;

linear or branched hydrocarbons, of mineral or synthetic origin, such as volatile or non-volatile liquid paraffins, and derivatives thereof, petroleum jelly, polydecenes, isohexadecane, isododecane, hydrogenated polyisobutene such as Parleam oil, or the mixture of n-undecane (C11) and of n-tridecane (C13) sold under the reference Cetiol UT by the company Cognis;

fluoro oils that are partially hydrocarbon-based and/or silicone-based, for instance those described in document JP-A-2 295 912;

silicone oils, for instance volatile or non-volatile polymethylsiloxanes (PDMS) with a linear or cyclic silicone chain, which are liquid or pasty at room temperature, in particular volatile silicone oils, especially cyclopolydimethylsiloxanes (cyclomethicones) such as cyclohexadimethylsiloxane and cyclopentadimethylsiloxane; polydimethylsiloxanes comprising alkyl, alkoxy or phenyl groups, which are pendent or at the end of a silicone chain, these groups containing from 2 to 24 carbon atoms; phenyl silicones, for instance phenyl trimethicones, phenyl dimethicones, phenyltrimethylsiloxy-diphenyl-siloxanes, diphenyl dimethicones, diphenylmethyldiphenyltrisiloxanes or 2-phenylethyl trimethylsiloxy silicates, and polymethylphenylsiloxanes;

mixtures thereof.

In the list of oils mentioned above, the term "hydrocarbon-based oil" means any oil mainly comprising carbon and hydrogen atoms, and possibly ester, ether, fluoro, carboxylic acid and/or alcohol groups.

The other fatty substances that may be present in the oily phase are, for example, fatty acids containing from 8 to 30 carbon atoms, for instance stearic acid, lauric acid, palmitic acid and oleic acid; waxes, for instance lanolin wax, beeswax, carnauba wax or candelilla wax, paraffin wax, lignite wax or microcrystalline waxes, ceresin or ozokerite, and synthetic waxes, for instance polyethylene waxes and Fischer-Tropsch waxes; silicone resins such as trifluoromethyl-C1-4-alkyl dimethicone and trifluoropropyl dimethicone; and silicone elastomers, for instance the products sold under the name KSG by the company Shin-Etsu, under the name Trefil, BY29 or EPSX by the company Dow Corning, or under the name Gransil by the company Grant Industries.

These fatty substances may be chosen in a varied manner by a person skilled in the art so as to prepare a composition having the desired properties, for example in terms of consistency or texture.

The emulsions generally contain at least one emulsifier chosen from amphoteric, anionic, cationic and nonionic emulsifiers, used alone or as a mixture, and optionally a co-emulsifier. The emulsifiers are chosen in an appropriate manner according to the emulsion to be obtained (W/O or O/W). The emulsifier and the co-emulsifier are generally present in the composition in a proportion ranging from 0.3% to 30% by weight and preferably from 0.5% to 20% by weight relative to the total weight of the composition.

For W/O emulsions, examples of emulsifiers that may be mentioned include dimethicone copolyols, such as the mixture of cyclomethicone and dimethicone copolyol sold under the trade name DC 5225 C by the company Dow Corning, and alkyl dimethicone copolyols such as the lauryl dimethicone copolyol sold under the name Dow Corning 5200 Formulation Aid by the company Dow Corning, and the cetyl dimethicone copolyol sold under the name Abil EM 90® by the company Goldschmidt. A crosslinked elastomeric solid organopolysiloxane comprising at least one oxyalkylene group, such as those obtained according to the procedure of Examples 3, 4 and 8 of U.S. Pat. No. 5,412,004 and of the examples of U.S. Pat. No. 5,811,487, especially the product of Example 3 (synthesis example) of U.S. Pat. No. 5,412,004, such as the product sold under the reference KSG 21 by the company Shin-Etsu, may also be used as surfactants for W/O emulsions.

For O/W emulsions, examples of emulsifiers that may be mentioned include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters; oxyalkylenated (oxyethylenated and/or oxypropylenated) fatty alcohol ethers; sugar esters such as sucrose stearate; and mixtures thereof, such as the mixture of glyceryl stearate and PEG-40 stearate.

These compositions may also be O/W emulsions stabilized with particles, for instance the polymer particles described in patent FR 2 760 641, or crosslinked or non-crosslinked amphiphilic polymers, as described in patent applications FR 2 853 543 and FR 2 819 175.

In a known manner, the cosmetic composition may also contain adjuvants that are common in cosmetics, such as hydrophilic or lipophilic gelling agents, hydrophilic or lipophilic active agents, preserving agents, antioxidants, solvents, fragrances, fillers, odour absorbers and dyestuffs. The amounts of these various adjuvants are those conventionally used in the cosmetics field, and range, for example, from about 0.01% to 10% of the total weight of the composition. Depending on their nature, these adjuvants may be introduced into the fatty phase, into the aqueous phase and/or into lipid spherules.

As solvents that may be used in the invention, mention may be made of lower alcohols, for instance ethanol, isopropanol, dipropylene glycol, butylene glycol and propylene glycol.

As hydrophilic gelling agents that may be used in the invention, non-limiting examples that may be mentioned include carboxyvinyl polymers (Carbomer®), acrylic copolymers such as acrylate/alkylacrylate copolymers, polyacrylamides, polysaccharides such as hydroxypropylcellulose, natural gums and clays, and lipophilic gelling agents that may be mentioned include modified clays such as bentones, metal salts of fatty acids, for instance aluminium stearates, hydrophobic silica, ethylcellulose and polyethylene.

When the monosaccharide is administered orally, the composition containing it may advantageously be in the form of a gel capsule, a tablet or pills. When the monosaccharide is administered via cutaneous injection, the composition containing it may be in particular in the form of a sterile solution.

The compositions of the invention may contain other hydrophilic or lipophilic active agents. These active agents are chosen especially from antioxidants, dermo-relaxing or dermo-decontracting agents, anti-ageing agents, anti-glycation agents, agents for stimulating the synthesis of dermal or epidermal macromolecules and/or for preventing their degradation, agents for stimulating fibroblast or keratinocyte proliferation and/or keratinocyte differentiation, agents for promoting maturation of the horny envelope, NO-synthase inhibitors, and agents for stimulating the energy metabolism of cells.

Anti-Ageing Agents:

Among the active agents that are known for combating the signs of ageing, especially ageing of the skin, mention may be made especially of:

vitamin B3, coenzyme Q10 (or ubiquinone), vitamin B9, vitamin E, vitamin E derivatives, such as the phosphate derivative, for instance TPNA® sold by the company Showa Denko, resveratrol or derivatives thereof, for instance Resveratrate® sold by the company Estée Lauder, retinol or derivatives thereof, and a mixture thereof.

Anti-Glycation Agents:

The term "anti-glycation agent" means a compound that prevents and/or reduces the glycation of skin proteins, in particular dermal proteins such as collagen.

Anti-glycation agents that may especially be mentioned include extracts of plants of the Ericacea family, such as an extract of blueberry (*Vaccinium angustifolium* or *Vaccinium myrtillus*), for example the product sold under the name Blueberry Herbasol Extract PG by the company Cosmetochem, ergothioneine and derivatives thereof, hydroxystilbenes and derivatives thereof, such as resveratrol and 3,3',5,5'-tetrahydroxystilbene (these anti-glycation agents are described in patent applications FR 2 802 425, FR 2 810 548, FR 2 796 278 and FR 2 802 420, respectively), dihydroxystilbenes and derivatives thereof, polypeptides of arginine and of lysine such as the product sold under the name Amadorine® by the company Solabia, carcinine hydrochloride (sold by Exsymol under the name Alistin®), an extract of *Helianthus annuus*, for instance Antiglyskin® from Silab, wine extracts such as the extract of powdered white wine on a maltodextrin support sold under the name Vin blanc déshydraté 2F by the company Givaudan, thioctic acid (or alpha-lipoic acid), a mixture of extract of bearberry and of marine glycogen, for instance Aglycal LS 8777® from Laboratoires Sérobiologiques, and an extract of black tea, for instance Kombuchka® from Sederma, and mixtures thereof.

Preferred anti-glycation agents that will be mentioned include extracts of blueberry (*Vaccinium myrtillus*) and extracts of black tea.

Agents for Stimulating the Synthesis of Dermal and/or Epidermal Macromolecules and/or for Preventing their Degradation Among the active agents for stimulating the dermal macromolecules or for preventing their degradation, mention may be made of those acting:

either on collagen synthesis, such as extracts of *Centella asiatica*, asiaticosides and derivatives thereof; synthetic peptides such as iamin, biopeptide CL or palmitoyl oligopeptide sold by the company Sederma; peptides extracted from plants, such as the soybean hydrolysate sold by the company Coletica under the trade name Phytokine®; rice peptides such as Nutripeptide® from Silab, methylsilanol mannuronate such as Algisium C® sold by Exsymol; plant hormones such as auxins and lignans; folic acid; and an extract of *Medicago sativa* (alfalfa) such as the product sold by Silab under the name Vitanol®; a peptide extract of hazelnut such as the product sold by the company Solabia under the name Nuteline C®; and arginine;

or on the inhibition of collagen degradation, in particular agents acting on the inhibition of metalloproteases (MMP) more particularly such as MMP 1, 2, 3 and 9. Mention may be made of: retinoids and derivatives, extracts of *Medicago sativa* such as Vitanol® from Silab, an extract of *Aphanizomenon flos-aquae* (Cyanophyceae) sold under the name Lanablue® by Atrium Biotechnologies, oligopeptides and lipopeptides, lipoamino acids, the malt extract sold by the company Coletica under the trade name Collalift®; blueberry or rosemary extracts; lycopene; isoflavones, derivatives thereof or plant extracts containing them, in particular extracts of soybean (sold, for example, by the company Ichimaru Pharcos under the trade name Flavosterone SB®), of red clover, of flax or of kakkon; an extract of lychee; Dipalmitoyl Hydroxyproline sold by SEPPIC under the name Sepilift DPHP®; *Baccharis genistelloides* or Baccharine sold by Silab, an extract of *moringa* such as Arganyl LS 9781® from Cognis; the sage extract described in patent application FR-A-2 812 544 from the Labiatae family (*Salvia officinalis* from the company Flacksmann), an extract of rhododendron, a blueberry extract, and an extract of *Vaccinium myrtillus* such as those described in patent application FR-A-2 814 950;

or on the synthesis of molecules belonging to the elastin family (elastin and fibrillin), such as: retinol and derivatives, in particular retinyl palmitate; the extract of *Saccharomyces cerevisiae* sold by the company LSN under the trade name Cytovitin®; and the extract of the alga *Macrocystis pyrifera* sold by the company Secma under the trade name Kelpadelie®; a peptide extract of hazelnut such as the product sold by the company Solabia under the trade name Nuteline C®;

or on inhibition of elastin degradation, such as the peptide extract of seeds of *Pisum sativum* sold by the company LSN under the trade name Parelastyl®; heparinoids; and the N-acylamino amide compounds described in patent application WO 01/94381, such as {2-[acetyl(3-trifluoromethylphenyl)amino]-3-methylbutyrylamino}acetic acid, also known as N—[N-acetyl, N'-(3-trifluoromethyl)phenylvalyl]glycine, or N-acetyl-N-[3-(trifluoromethyl)phenyl]valylglycine or acetyl trifluoromethylphenylvalylglycine, or an ester thereof with a $C_1$-$C_6$ alcohol; an extract of rice peptides such as Colhibin® from Pentapharm, or an extract of *Phyllanthus emblica* such as Emblica® from Rona;

or on the synthesis of glycosaminoglycans, such as the product of fermentation of milk with *Lactobacillus vulgaris*, sold by the company Brooks under the trade name Biomin Yoghurt®; the extract of the brown alga *Padina pavonica* sold by the company Alban Müller under the trade name HSP3®; the *Saccharomyces cerevisiae* extract available especially from the company Silab under the trade name Firmalift® or from the company LSN under the trade name Cytovitin®; an extract of *Laminaria ochroleuca* such as Laminaine® from Secma; essence of Mamaku from Lucas Meyer, and an extract of Cress (Odraline® from Silab);

or on the synthesis of fibronectin, such as the extract of the zooplankton Salina sold by the company Seporga under the trade name GP4G®; the yeast extract available especially from the company Alban Müller under the trade name Drieline®; and the palmitoyl pentapeptide sold by the company Sederma under the trade name Matrixyl®.

Among the active agents for stimulating epidermal macromolecules, such as fillagrin and keratins, mention may be made especially of the extract of lupin sold by the company Silab under the trade name Structurine®; the extract of *Fagus sylvatica* beech buds sold by the company Gattefosse under the trade name Gatuline® RC; and the extract of the zooplankton Salina sold by the company Seporga under the trade name GP4G®; the copper tripeptide from Procyte; a peptide extract of *Voandzeia substerranea* such as the product sold by the company Laboratoires Sérobiologiques under the trade name Filladyn LS 9397®.

Preferably, an active agent that stimulates the synthesis of dermal and/or epidermal macromolecules and/or that prevents their degradation, chosen from agents for stimulating the synthesis of glycosaminoglycans, agents for inhibiting elastin degradation, agents for stimulating fibronectin synthesis, agents for stimulating the synthesis of epidermal macromolecules, and mixtures thereof, will be used.

Even more preferentially, an active agent that stimulates the synthesis of the glycosaminoglycans, chosen from an extract of the brown alga *Padina pavonica*, an extract of *Saccharomyces cerevisiae*, an extract of *Laminaria ochroleuca*, essence of Mamaku, and an extract of cress, and mixtures thereof, will be used.

As preferred active agents for stimulating the synthesis of dermal and/or epidermal macromolecules and/or for preventing their degradation, mention may be made of:

synthetic peptides such as iamin, the biopeptide CL or palmitoyloligopeptide sold by the company Sederma; peptides extracted from plants, such as the soybean hydrolysate sold by the company Coletica under the trade name Phytokine®; rice peptides such as Nutripeptide® from Silab, methylsilanol mannuronate such as Algisium C® sold by Exsymol; folic acid; an extract of *Medicago sativa* (alfalfa), such as the product sold by Silab under the name Vitanol®; a peptide extract of hazelnut, such as the product sold by the company Solabia under the name Nuteline C®; arginine; an extract of *Aphanizomenon flos-aquae* (Cyanophyceae) sold under the name Lanablue® by Atrium Biotechnologies, the malt extract sold by the company Coletica under the trade name Collalift®, lycopene; an extract of lychee; an extract of *moringa* such as Arganyl LS 9781® from Cognis; an extract of *Vaccinium myrtillus* such as those described in patent application FR-A-2 814 950; retinol and derivatives thereof, in particular retinyl palmitate; the extract of *Saccharomyces cerevisiae* sold by the company LSN under the trade name Cytovitin®; a peptide extract of hazelnut such as the product sold by the company Solabia under the name Nuteline C®; {2-[acetyl(3-trifluoromethylphenyl)amino]-3- methylbutyrylamino}acetic acid, also known as N—[N-acetyl, N'-(3-trifluoromethyl)phenylvalyl]glycine, or N-acetyl-N-[3-(trifluoromethyl)phenyl]valylglycine or acetyl trifluoromethylphenylvalylglycine, or an ester thereof with a $C_1$-$C_6$ alcohol; an extract of rice peptides such as Colhibin® from Pentapharm, or an extract of *Phyllanthus emblica* such as Emblica® from Rona; the extract of the brown alga *Padina pavonica* sold by the company Alban Müller under the trade name HSP3®; the extract of *Saccharomyces cerevisiae* available especially from the company Silab under the trade name Firmalift® or from the company LSN under the trade name Cytovitin®; an extract of *Laminaria ochroleuca* such as Laminaine® from Secma; the essence of Mamaku from Lucas Meyer, the extract of lupin sold by the company Silab under the trade name Structurine®; the extract of *Fagus sylvatica* beech buds sold by the company Gattefosse under the trade name Gatuline® RC.

Agents for Stimulating Fibroblast or Keratinocyte Proliferation and/or Keratinocyte Differentiation The agents for stimulating fibroblast proliferation that may be used in the composition according to the invention may be chosen, for example, from plant proteins or polypeptides, extracted especially from soybean (for example a soybean extract sold by the company LSN under the name Eleseryl SH-VEG 8® or sold by the company Silab under the trade name Raffermine®); an extract of hydrolysed soybean proteins such as Ridulisse® from Silab; and plant hormones such as gibberellins and cytokinins; a peptide extract of hazelnut such as the product sold by the company Solabia under the name Nuteline C®.

Preferably, an agent that promotes keratinocyte proliferation and/or differentiation will be used.

The agents for stimulating keratinocyte proliferation that may be used in the composition according to the invention especially comprise phloroglucinol, the extract of *Hydrangea macrophylla* leaves, for instance Amacha Liquid E® from Ichimaru Pharcos, a yeast extract such as Stimoderm® from CLR; the extract of *Larrea divaricata* such as Capislow® from Sederma, mixtures of extract of papaya, of olive leaves and of lemon, such as Xyleine® from Vincience, retinol and esters thereof, including retinyl palmitate, phloroglucinol, the nut cake extracts sold by the Gattefosse and the extracts of *Solanum tuberosum* such as Dermolectine® sold by Sederma.

Among the agents for stimulating keratinocyte differentiation are, for example, minerals such as calcium; a peptide extract of lupin, such as the product sold by the company Silab under the trade name Structurine®; sodium beta-sitosteryl sulfate, such as the product sold by the company Seporga under the trade name Phytocohesine®; and a water-soluble extract of corn, such as the product sold by the company Solabia under the trade name Phytovityl®; a peptide extract of *Voandzeia substerranea* such as the product sold by the company Laboratoires Sérobiologiques under the trade name Filladyn LS 9397®; and lignans such as secoisolariciresinol, and retinol and esters thereof, including retinyl palmitate.

As agents for stimulating keratinocyte proliferation and/or differentiation, mention may also be made of oestrogens such as oestradiol and homologues; or cytokines.

As preferred active agents for stimulating fibroblast or keratinocyte proliferation and/or keratinocyte differentiation, mention will be made of plant proteins or polypeptides, extracted especially from soybean (for example a soybean extract sold by the company LSN under the name Eleseryl SH-VEG 8® or sold by the company Silab under the trade name Raffermine®); an extract of hydrolysed soybean proteins such as Ridulisse® from Silab; a peptide extract of hazelnut such as the product sold by the company Solabia under the name Nuteline C®; phloroglucinol, a yeast extract such as Stimoderm® from CLR; a peptide extract of lupin such as the product sold by the company Silab under the trade name Structurine®; a water-soluble corn extract, such as the product sold by the company Solabia under the trade name Phytovityl®; a peptide extract of *Voandzeia substerranea*, such as the product sold by the company Laboratoires Sérobiologiques under the trade name Filladyn LS 9397®; retinol and esters thereof, including retinyl palmitate.

Agents for Promoting the Maturation of the Horny Envelope

Agents that participate in the maturation of the horny envelope, which becomes impaired with age and induces a decrease in transglutaminase activity, may be used in the compositions of the invention. Examples that may be mentioned include urea and derivatives thereof and in particular Hydrovance® from National Starch and the other active agents mentioned in L'Oréal patent application FR 2 877 220.

NO-Synthase Inhibitors

The agent with an inhibitory action on NO synthase may be chosen from OPCs (procyannidol oligomers); plant extracts of the species *Vitis vinifera* sold especially by the company Euromed under the name "Leucocyanidines de raisins extra", or by the company Indena under the name Leucoselect®, or finally by the company Hansen under the name "Extrait de marc de raisin"; plant extracts of the species *Olea europaea* preferably obtained from olive tree leaves and sold especially by the company Vinyals in the form of a dry extract, or by the company Biologia & Technologia under the trade name Eurol® BT; and plant extracts of the species *Gingko biloba*, preferably a dry aqueous extract of this plant sold by the company Beaufour under the trade name "Ginkgo biloba extract standard", and mixtures thereof.

Agents for Stimulating the Energy Metabolism of Cells

The active agent for stimulating the energy metabolism of cells may be chosen, for example, from biotin, an extract of *Saccharomyces cerevisiae* such as Phosphovital® from Sederma, the mixture of sodium, manganese, zinc and magnesium salts of pyrrolidonecarboxylic acid, for instance Physiogenyl® from Solabia, a mixture of zinc, copper and magnesium gluconate, such as Sepitonic M3® from SEPPIC, and mixtures thereof; a beta-glucan derived from *Saccharomyces cerevisiae*, such as the product sold by the company Mibelle AG Biochemistry.

The monosaccharide according to the invention may be applied to the part of the skin or integuments to be treated, in particular to the face, the neck, the hands, the hair or the scalp, preferably daily or several times a day. The application will, for example, be repeated every day over a variable period according to the desired effects, generally from 3 to 6 weeks, but may be prolonged or pursued continuously.

According to one alternative, the monosaccharide according to the invention or the compositions containing it may be administered by injection optionally in combination with filling products. Specifically, one of the solutions adopted for combating wrinkles and/or the loss of volume of soft tissue is the use of filling products (or filler). This filling may be achieved by using non-resorbable products, such as polyacrylamide gels or polymethyl methacrylate (PMMA) particles. However, these compounds may lead to intolerance reactions of the type such as inflammation or hypersensitivity.

The use of resorbable components, such as proteins, fats, collagen or hyaluronic acid, is preferred. However, these compounds are degraded relatively quickly in the body, which reduces their efficacy. To overcome this, more or less expensive crosslinking of these components must be performed.

At the present time, the hyaluronic acid used in pharmaceutical forms or medical devices is in the form of a sodium hyaluronate gel.

The monosaccharide according to the invention or the compositions containing it may also be applied by mesotherapy.

Mesotherapy is a technique of treatment via intraepidermal and/or intradermal and/or subcutaneous injection of active product(s), for instance micronutrients, vitamins and/or hyaluronic acid. The compositions are administered according to this technique via injection in the form of multiple small droplets into the epidermis, the dermo-epidermal junction and/or the dermis in order especially to perform subcutaneous layering. The mesotherapy technique is especially described in the publication "Traité de mésothérapie" by Jacques Le Coz, published by Masson, 2004.

Mesotherapy performed on the face is also referred to as a mesolift or a mesoglow.

Thus, another object of the present invention may be a device, in particular a medical device, comprising at least one monosaccharide as defined above, the device being suitable for intraepidermal and/or intradermal and/or subcutaneous injection. The said monosaccharide is preferably in combination with a sterile solution. The said device may comprise at least one other compound, for instance at least one resorbable or non-resorbable product, such as those mentioned above, which is optionally crosslinked.

The said device may be, for example, a syringe with a needle or an injection device without a needle, such as those used in the care technique known as mesotherapy. A kit comprising a device may also be envisaged, the said kit comprising a device, in particular a syringe or an injection device, and at least one monosaccharide as defined above. The said kit may also comprise a needle. The said device may be in ready-to-use form, i.e. prefilled, or may need to be filled before use. In the latter case, a composition or another device (such as a vial) comprises the said monosaccharide, optionally in combination with at least one other active compound, for instance at least one resorbable or non-resorbable product, such as the filling products mentioned above, which is optionally crosslinked.

The injection of the monosaccharide according to the invention may be performed simultaneously with, or before or after, the application to the skin or the integuments of another cosmetic or pharmaceutical composition, preferably a dermatological composition, comprising, in a physiologically acceptable support, at least one other active agents, as mentioned above.

KEY TO THE FIGURES

Figure 1:
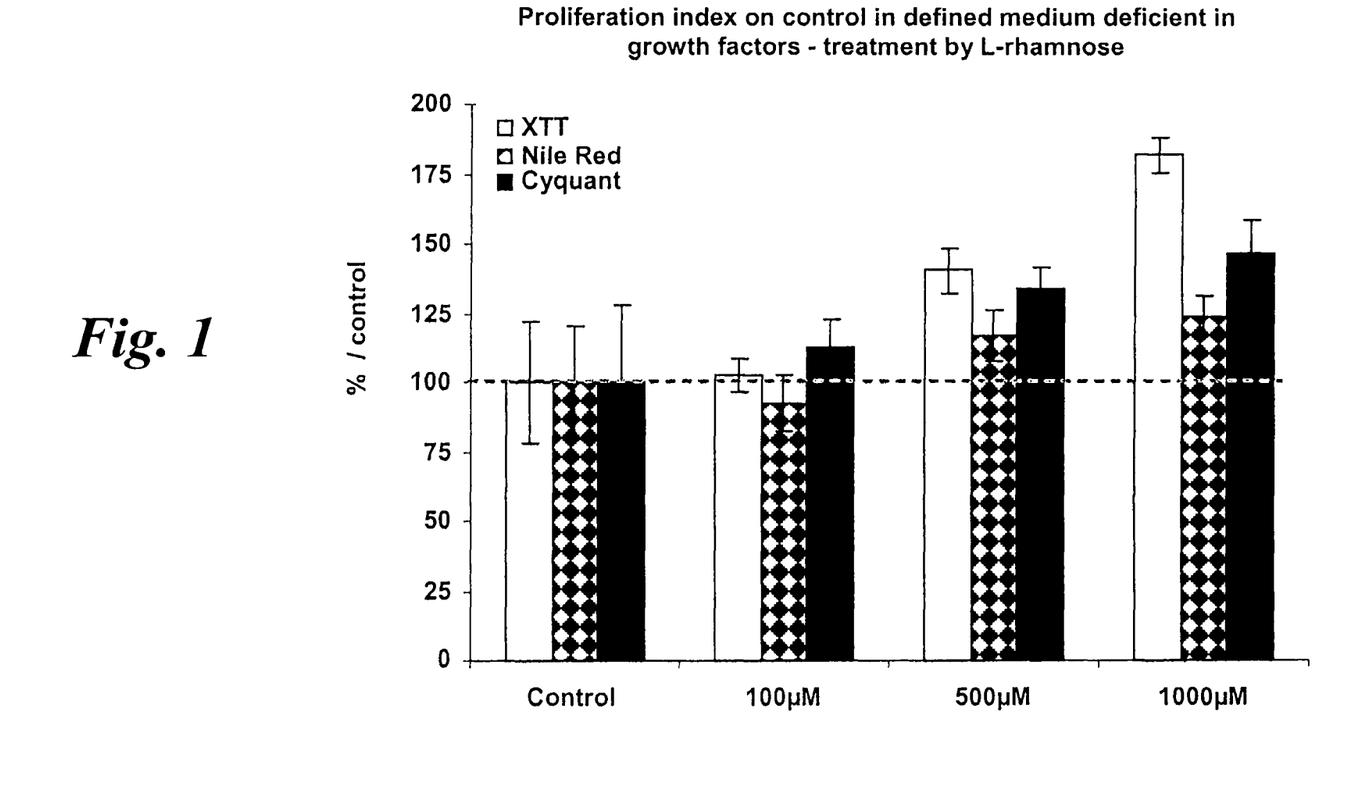
FIG. 1 shows the results obtained for the keratinocyte proliferation under certain conditions, described in detail below.

FIG. 1: Diagram schematically representing the results obtained for the keratinocyte proliferation, in the presence of a control, in the presence of different markers, in medium deficient in growth factors, and with addition of different concentrations of L-rhamnose reported on the x-axis. The values reported on the y-axis correspond to the percentages of labelled cells measured relative to the control.

Figure 2:
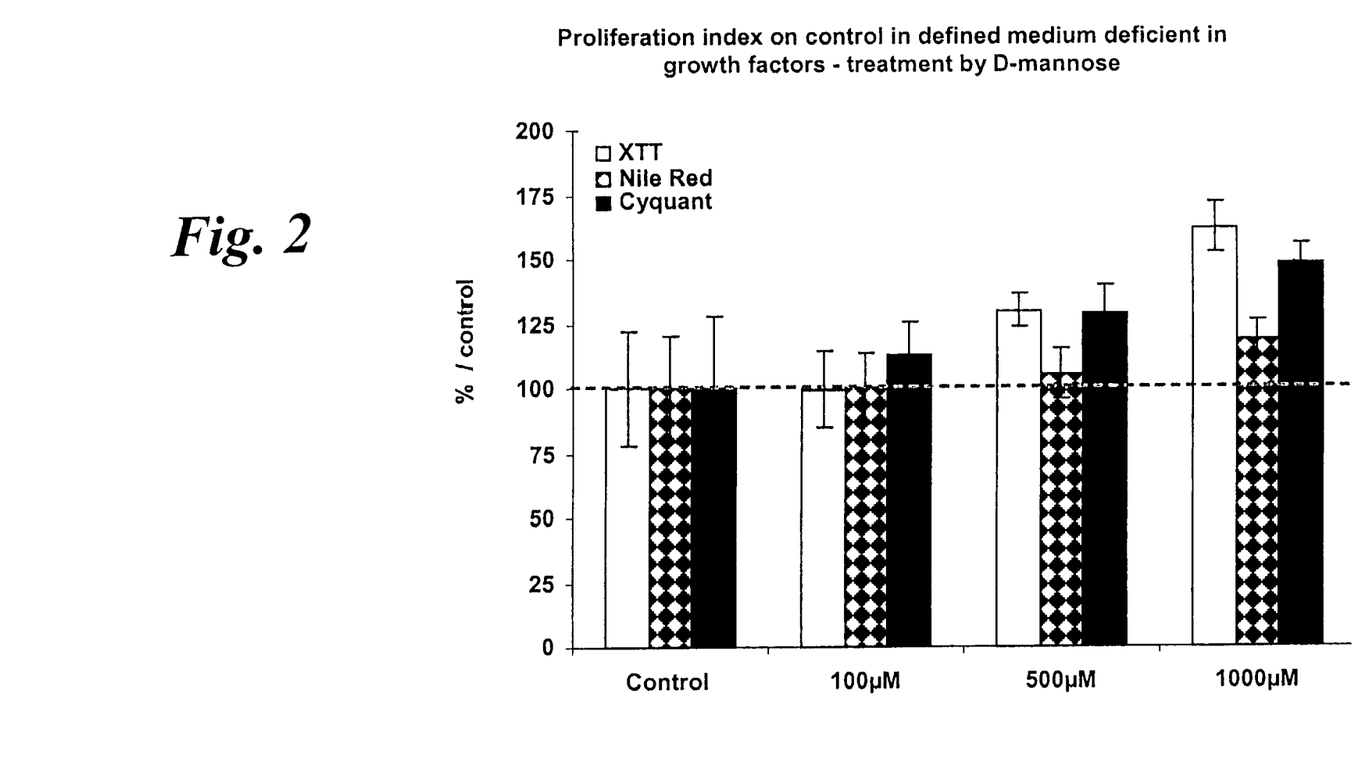
FIG. 2 shows the results obtained for the keratinocyte proliferation under certain conditions, described in detail below.

FIG. 2: Diagram schematically representing the results obtained for the keratinocyte proliferation, in the presence of a control, in the presence of different markers, in medium deficient in growth factors, and with addition of different concentrations of D-mannose reported on the x-axis. The values reported on the y-axis correspond to the percentages of labelled cells measured relative to the control.

Figure 3:
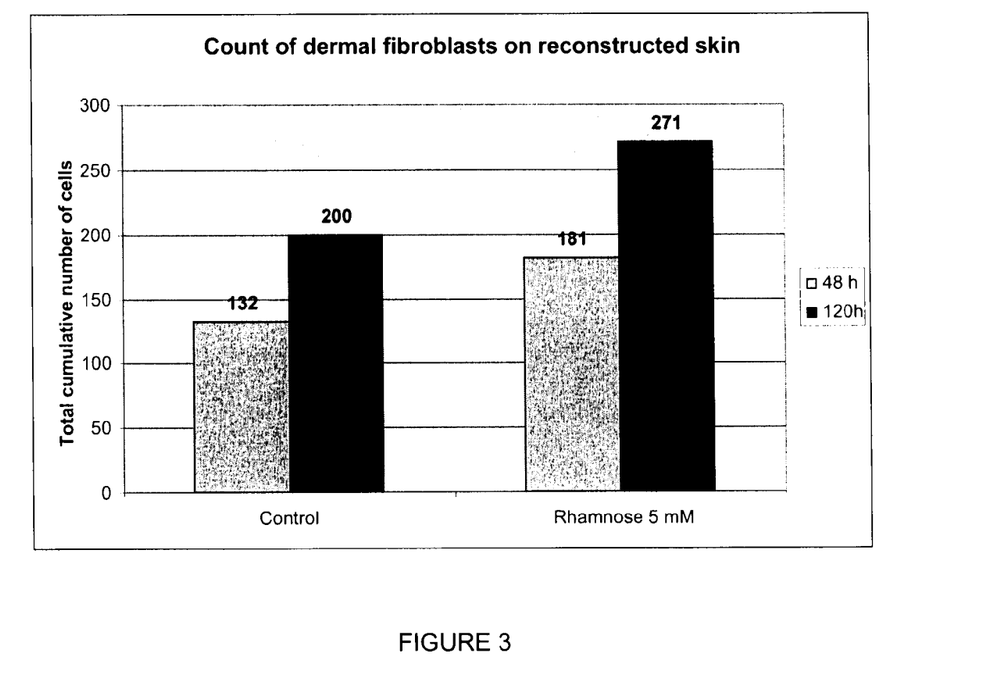
FIG. 3 shows the number of fibroblasts measured between an untreated control whole reconstructed skin, on the left, and a whole reconstructed skin treated with 5 mM of rhamnose, on the right.

FIG. 3: Diagram representing the number of fibroblasts measured between an untreated control whole reconstructed skin, on the left, and a whole reconstructed skin treated with 5 mM of rhamnose, on the right. The fibroblasts are counted at different stages of the treatment. Thus, for each skin type, the left-hand column corresponds to the count obtained at 48 hours and the right-hand column corresponds to the count obtained at 120 hours of treatment.

Figure 4:
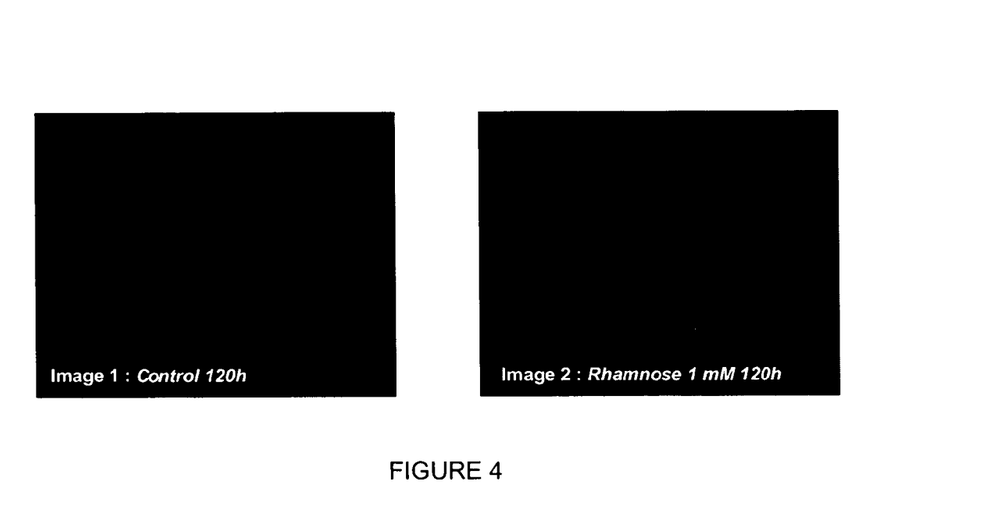
FIG. 4 shows frozen sections of reconstructed skin 7 μm thick.

FIG. 4: images of frozen sections of reconstructed skin 7 μm thick. The level of fluorescence is materialized by the white marks on the black and white image; it is proportional to the amount of type I procollagen. The control skin is on the left, and skin treated with 1 mM of rhamnose is on the right.

The invention is illustrated in greater detail in the examples that follow, which are given as non-limiting illustrations of the field of the invention.

EXAMPLES

Example 1

Proliferation of Keratinocytes

Protocol

The keratinocytes (HaCat line) are cultured under two conditions: whole defined culture medium (standard condition) and culture medium deficient in growth factors. This deficient medium gives rise to a controlled delay in cell proliferation. Under these conditions, it is then possible to measure the effects of compounds capable of compensating for the deficiency in growth factors of the culture medium and thus of relaunching the cell multiplication and/or of stimulating cell metabolism.

The keratinocyte proliferation is measured by means of three markers on the same cell population: the level of DNA, which is proportional to the number of cells (Cyquant probe), the level of constituent polar lipids of cell membranes (Nile red probe) and the mitochondrial respiration, which reflects the general cell metabolism (XTT probe).

Results

The results are given in FIGS. 1 and 2.

The two monosaccharides rhamnose and mannose demonstrate their capacity to activate keratinocyte proliferation when the keratinocytes are cultured in medium depleted in growth factors, a culturing condition that significantly delays their cell growth.

This activation of cell proliferation by the two compounds is manifested by a higher number of cells when compared with the untreated control.

This increased number of cells is materialized by a level of DNA (Cyquant), a level of polar lipids (Nile red signal) and a mitochondrial respiration (XTT signal) that are significantly increased when the monosaccharides are evaluated at 1 mM. At 500 μM, the two molecules already show efficacy. The two monosaccharides mannose and rhamnose thus exert an influence on keratinocyte proliferation. They activate the proliferation of keratinocytes cultured in medium depleted in growth factor, which is manifested by a higher number of cells when compared with an untreated control.

Rhamnose and mannose thus show anti-ageing efficacy by boosting epidermal renewal and combating age-related epidermal atrophy.

Example 2

Proliferation of Fibroblasts

Protocol

Rhamnose was studied on a model of whole reconstructed skin in order to measure its anti-ageing efficacy on the dermal compartment.

Briefly, the model of reconstructed skin used is that described by Bell et al. (Bell E. et al., *The reconstitution of living skin, J. Invest. Dermatol.*, 1983, July; 81): it includes a dermal equivalent on which is reconstructed a multistratified epidermis; the dermal equivalent is manufactured from acid-soluble collagen, culture medium containing serum and normal adult human fibroblasts. After 5 days of shrinkage, this equivalent is inoculated with keratinocytes and then cultured for 6 days in immersion and for 7 days in emersion in order to obtain a multistratified and differentiated epidermis having a horny layer.

The reconstructed skin is treated with 5 mM rhamnose for 2 days and 5 days in the culture medium; after the treatment, the reconstructed skins are included in Tissue Tek in order to produce frozen sections 7 μm thick with a cryostat. The sections produced are then stained with propidium iodide to label the DNA of the nuclei of the fibroblasts in order to count them. Three frozen sections are prepared at random on each reconstructed skin; on each section, two microscopic fields (25× objective lens) are analysed by fluorescence microscopy and photographed. The dermal fibroblasts are thus counted for each reconstructed skin on six images in total representing the six microscopic fields considered. The number of dermal fibroblasts is compared between the control skin and that treated with rhamnose at the two kinetic stages.

Results

The results are given in FIG. 3.

It was found that rhamnose induces stimulation of growth of the dermal fibroblasts of the reconstructed skin within 48 hours of treatment, this stimulation being confirmed at 120 hours of treatment, with between 30% and 35% additional cells (see FIG. 3). It should be noted that this stimulation is accompanied by a stimulation of procollagen 1 synthesis at 5 mM, and also at 1 mM, which may also result from the increased number of fibroblasts responsible for the secretion of this major protein of the extracellular matrix.

These two effects complement the anti-ageing activity of rhamnose already measured on the epidermal compartment, by stimulating the proliferation and metabolism of the fibroblast, which is a major cell of the dermal compartment.

Example 3

Synthesis of Procollagen 1

Conventional detection via indirect immunofluorescence of type I procollagen in the dermis of the reconstructed skin was also performed on other series of frozen sections (anti-procoll 1 antibody (MAB 1912 Millipore)+FTIC-coupled conjugate (112-095-068 Jackson Immunoresearch)). In order to obtain bearings within the cutaneous architecture during the microscopic examination of the sections, the cell nuclei of the keratinocytes and fibroblasts are localized by staining them with propidium iodide, as described above. Three frozen sections are prepared at random on each reconstructed skin and on each section, and two microscopic fields (25× objective lens) are analysed by fluorescence microscopy and photographed. The levels of fluorescence proportional to the amount of type I procollagen are compared between the control skin and the skin treated with rhamnose.

In image 1, FIG. 4, corresponding to a section of control reconstructed skin at 120 hours of culture, the presence of type 1 procollagen synthesized by the dermal fibroblasts is materialized by the green fluorescence located in the bottom part of the image. The basal part of the epidermis, highly cellular tissue, which may be visualized by the numerous keratinocyte nuclei, can be made out in the top part of the image. The dermis, much less cellular tissue, also reveals the random distribution of the fibroblasts within the dermal extracellular matrix.

In image 2, FIG. 4, corresponding, for example, to a section of reconstructed skin treated with 1 mM rhamnose for 120 hours, a marked increase in green fluorescence is noted when compared with that observed for the control skin (image 1), and also a distribution of the fluorescent signal clearly materializing the fibrillar aspect of the newly synthesized type I procollagen. This increase in general fluorescence indicates that the rhamnose treatment has greatly stimulated the synthesis of type I procollagen by the fibroblasts.

These results clearly show the capacity of rhamnose to stimulate fibroblast metabolism, which metabolism, in the course of ageing, becomes more imbalanced towards degradation of the extracellular matrix than towards its renewal.

By stimulating both the metabolism and growth of dermal fibroblasts, rhamnose clearly demonstrates its anti-ageing efficacy on the dermis, this efficacy being complementary to that measured with respect to the epidermal compartment.

Example 4

Cosmetic Compositions

Composition A

| Epidermal and dermal regenerating creams:<br>oil-in-water emulsion | Comp. A |
|---|---|
| Ammonium Polyacryldimethyltauramide (Hostacerin AMPS from Clariant) | 1.00% |
| Cyclohexasiloxane | 5.0% |
| Glycerol | 1.70% |
| Stearyl alcohol | 0.30% |
| Glyceryl stearate/PEG-100 stearate | 0.70% |
| Dimyristyl tartrate/cetearyl alcohol/C12-15 pareth-7/PPG-25 laureth-25 | 0.50% |
| Xanthan gum | 0.20% |
| Rhamnose | 5% |
| Preserving agents | 0.50% |
| Water | qs 100 |

Composition B

| Epidermal regeneration creams: oil-in-water emulsion | Comp. B |
|---|---|
| Ammonium Polyacryldimethyltauramide (Hostacerin AMPS from Clariant) | 1.00% |
| Cyclohexasiloxane | 5.0% |
| Glycerol | 1.70% |
| Stearyl alcohol | 0.30% |
| Glyceryl stearate/PEG-100 stearate | 0.70% |
| Dimyristyl tartrate/cetearyl alcohol/C12-15 pareth-7/PPG-25 laureth-25 | 0.50% |
| Xanthan gum | 0.20% |
| Mannose | 5% |
| Preserving agents | 0.50% |
| Water | qs 100 |

Composition C
Anti-Ageing Facial Day Cream
Phase A1:

| | |
|---|---|
| Sucrose distearate sold by the company Stearinerie Dubois | 1.75% |
| Sorbitan stearate oxyethylenated with 4 mol of ethylene oxide, sold by the company ICI under the name Tween 61 | 1.15% |
| Stearic acid | 0.75% |
| Stearyl heptanoate | 4.00% |
| Petroleum jelly codex | 1.50% |
| Avocado oil | 3.20% |
| Jojoba oil | 3.00% |
| Volatile silicone oil | 2.70% |
| Vitamin E acetate | 1.00% |
| Vitamin F glycerides | 3.00% |

Phase A2:

| | |
|---|---|
| Silicone gum sold by Dow Corning under the name Q2-1403 Fluid | 3.00% |
| Propyl paraben | 0.2% |
| Fragrance | 0.3% |

Phase B:

| | |
|---|---|
| Glycerol | 3.00% |
| Hydroxyproline | 1.00% |
| D-Panthenol | 1.00% |
| Triethanolamine | 0.35% |
| Rhamnose | 3.00% |
| Methyl paraben | 0.3% |
| Demineralized water | qs 100% |

Phase C:

| | |
|---|---|
| Ammonium Polyacryldimethyltauramide (Hostacerin AMPS from Clariant) | 1% |

Composition D
Anti-Ageing Nanoemulsions for the Face and Body
Oily Phase:

| | |
|---|---|
| Nikkol DGMS (Diglyceryl monostearate) (from Nikko) | 4% |
| Disodium salt of N-stearoyl-L-glutamic acid (Acylglutamate HS21 from the company Ajinomoto) | 0.5% |
| Jojoba oil (MW of about 900) | 6% |
| Volatile silicone oil | 6% |
| Isocetyl stearate (MW = 508) | 6% |

Aqueous Phase:

| | |
|---|---|
| Glycerol | 5% |
| Dipropylene glycol | 10% |
| Water | 55% |
| Mannose | 4% |

A transparent nanoemulsions is obtained.

The above written description of the invention provides a manner and process of making and using it such that any person skilled in this art is enabled to make and use the same, this enablement being provided in particular for the subject matter of the appended claims, which make up a part of the original description.

As used herein, the phrases "selected from the group consisting of," "chosen from," and the like include mixtures of the specified materials. Terms such as "contain(s)" and the like as used herein are open terms meaning 'including at least' unless otherwise specifically noted. The term "mentioned" notes exemplary embodiments, and is not limiting to certain species. As used herein the words "a" and "an" and the like carry the meaning of "one or more."

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

The invention claimed is:

1. A method of treating wrinkles and/or fine lines by increasing fibroblast proliferation, stimulating collagen synthesis or both, the method comprising applying to human skin in need thereof a composition comprising rhamnose in an amount of 0.5 to 10% by weight relative to the total weight of the composition, or a combination thereof, and wherein no tensioning agent is applied.

2. The method according to claim 1, wherein the rhamnose is present in an amount of 0.5% to 6% by weight relative to the total weight of the composition.

* * * * *